United States Patent [19]

Huang et al.

[11] Patent Number: 5,051,427

[45] Date of Patent: * Sep. 24, 1991

[54] QUINOLINE DERIVATIVES AS ANTAGONISTS OF LEUKOTRIENE $D_4$

[75] Inventors: Fu-Chi Huang, Gwynedd; Robert A. Galemmo, Jr., Ambler; Henry F. Campbell, North Wales, all of Pa.

[73] Assignee: Rhône-Poulenc Rorer Pharmaceuticals Inc., Fort Washington, Pa.

[ * ] Notice: The portion of the term of this patent subsequent to Apr. 17, 2007 has been disclaimed.

[21] Appl. No.: 449,957

[22] PCT Filed: Nov. 1, 1988

[86] PCT No.: PCT/US88/03895

§ 371 Date: Apr. 20, 1990

§ 102(e) Date: Apr. 20, 1990

[87] PCT Pub. No.: WO89/04303

PCT Pub. Date: May 18, 1989

Related U.S. Application Data

[63] Continuation-in-part of Ser. No. 116,428, Nov. 3, 1987, Pat. No. 4,920,133.

[51] Int. Cl.$^5$ .................... C07D 401/12; A61K 31/41
[52] U.S. Cl. .................................. 514/311; 546/176
[58] Field of Search ......................... 546/167; 514/314

[56] References Cited

U.S. PATENT DOCUMENTS

| | | | |
|---|---|---|---|
| 4,407,803 | 10/1983 | Haviv | 546/167 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |

Primary Examiner—David B. Springer
Attorney, Agent, or Firm—Martin F. Savitsky; James A. Nicholson; Alexis Barron

[57] ABSTRACT

This invention relates to certain quinoline–diaryl compounds and their use as leukotriene $D_4$ antagonists for the treatment of hypersensitive disorders.

22 Claims, No Drawings

QUINOLINE DERIVATIVES AS ANTAGONISTS OF LEUKOTRIENE $D_4$

CROSS REFERENCE TO RELATED APPLICATION

This is a continuation-in-part application of U.S. application Ser. No. 07/116,428, filed Nov. 3, 1987, now U.S. Pat. No. 4,920,133, issued Apr. 24, 1990.

FIELD OF INVENTION

This invention relates to quinolinyl phenylalkyl compounds and their use as valuable pharmaceutical agents, particularly as lipoxygenase inhibitors and/or leukotriene antagonists possessing anti-inflammatory and anti-allergic properties.

SUMMARY OF THE INVENTION

This invention relates to the compounds described by the general Formula I and to therapeutic compositions comprising as active ingredient a compound of Formula I:

Formula I

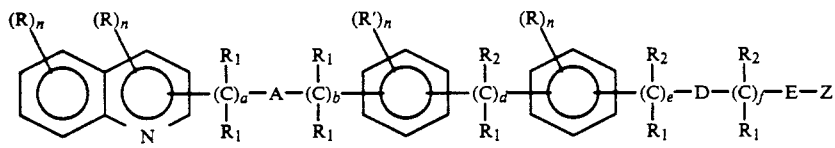

where:
A is O or S;

D is O, S, $NR_1$,

or a chemical bond
E is a chemical bond or

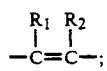

a is 0–2;
b is 0–1;
d is 1–5;
e is 0–4;
f is 0–5;
n is 0–2;
R is independently hydrogen, alkyl, hydroxy, alkoxy, carboxy, carbalkoxy, halo, nitro, haloalkyl, cyano or acyl;
R' is independently hydrogen, alkyl, hydroxy, alkoxy, halo or haloalkyl;
$R_1$ is independently hydrogen, alkyl or aralkyl;
$R_2$ is —$(CH_2)_x$—X;
x is 0–3;
X is hydrogen, alkyl, alkenyl, cycloalkyl, aryl, aralkyl, hydroxy, alkoxy, aralkoxy, amino, mono-and di-alkylamino, aralkylamino, acylamino, carbamyl, carboxy, carbalkoxy, tetrazolyl or acylsulfonamido;
vicinal $R_2$ groups together may be —$(CH_2)_y$—, where y is 1–4, thus forming a 3–6 membered ring;
geminal $R_1$ and $R_2$ groups may together form a spiro substituent, —$(CH_2)_z$—, where z is 2 to 5;
geminal $R_1$ or $R_1$ and $R_2$ groups may together form an alkylidenyl substituent, =$CHR_1$;
Z is —$COOR_1$, CN,

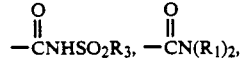

—$OR_1$, tetrazolyl or substituted tetrazolyl where the substituent may be alkyl, carboxyalkyl or carbalkoxyalkyl;
$R_3$ is hydrogen, alkyl, haloalkyl, phenyl or benzyl; and pharmaceutically acceptable salts thereof.

The compounds of Formula I contain at least three aromatic rings. For the purposes of this invention these may be designated as shown in Formula II. The substitution pattern of these rings along the chain with respect to each other is as follows.

Formula II

Ring I    Ring II    Ring III

The substitution pattern of the quinoline ring, that is Ring I, is preferably at the 2-position for extending the side chain. As this side chain progresses from the quinoline ring, the two phenyl rings, designated Ring II and Ring III may be substituted along the chain in the ortho, meta or para positions with respect to each other and Ring II may also be substituted in the ortho, meta and para positions in respect to the quinoline ring.

The preferred substitution pattern for Ring II is meta or para, that is:

IIIa

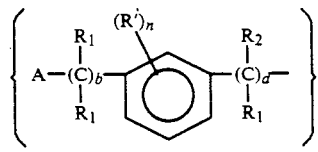

or

-continued

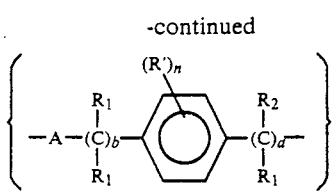
IIIb

Ring III however may be substituted equally in the ortho, metha or para positions, that is:

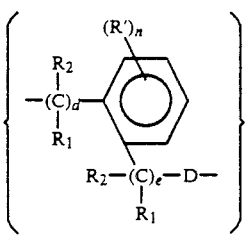
IVa

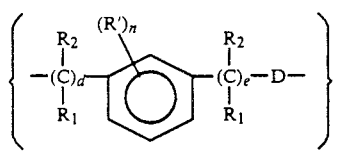
IVb or

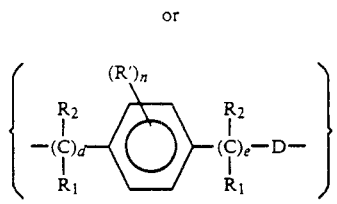
IVc

Further preferred compounds of this invention are described by Formula V below:

Formula V

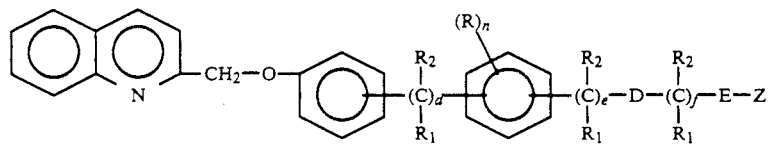

where
R, R, R, d, e, f, n, D, E and Z are as described above.
The more preferred compounds of Formula V are those where Z is —COOR$_1$; —CN;

or tetrazolyl.

In addition, the present invention relates to the method of using these compounds as lipoxygenase inhibitors and/or leukotriene antagonists possessing anti-inflammatory and anti-allergic properties.

As employed above and throughout the disclosure, the following terms, unless otherwise indicated, shall be understood to have the following meanings:

"Alkyl", either alone or with various substituents defined herein, means a saturated aliphatic hydrocarbon, either branched or straight chained. A "loweralkyl" is preferred having about 1 to about 6 carbon atoms. Examples of alkyl include methyl, ethyl, n-propyl, isopropyl, butyl, sec-butyl, t-butyl, amyl, hexyl, etc.

"Alkoxy" refers to a loweralkyl-O-group.

"Alkenyl" refers to a hydrocarbon having at least one point of unsaturation and may be branched or straight chained. Preferred alkenyl groups have six or less carbon atoms present such as vinyl, allyl, ethynyl, isopropenyl, etc.

"Aralkyl" means an alkyl group substituted by an aryl radical. The preferred aralkyl groups are benzyl or phenethyl.

"Cycloalkyl" means a saturated monocyclic hydrocarbon ring having 3 to about 6 carbon atoms such as cyclopropyl, cyclohexyl, etc.

"Acyl" means an organic radical derived from an organic acid by removal of its hydroxyl group. Preferred acyl groups are acetyl, propionyl, benzoyl, etc.

"Halo" means a halogen. Preferred halogens include, chloride, bromide and fluoride. The preferred haloalkyl group is trifluromethyl.

The compounds of this invention may be prepared in segments as is common to a long chain molecule. Thus it is convenient to synthesize these molecules by employing condensation reactions at the A and D cites of the molecule or at the bridge between the two phenyl rings. For this reason the present compounds may be prepared by art recognized procedures from known compounds or readily preparable intermediates. Exemplary general procedures are as follows where Z is —CN, —COOR$_1$ or tetrazolyl. Thus in order to prepare compound of formula I, the following reactions or combinations of reactions may be employed:

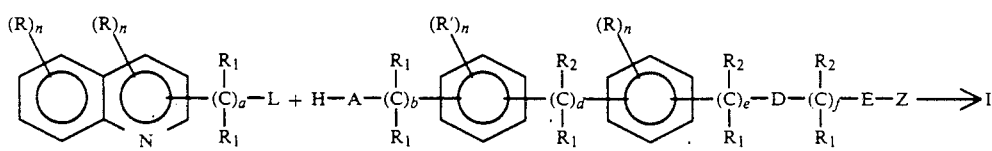

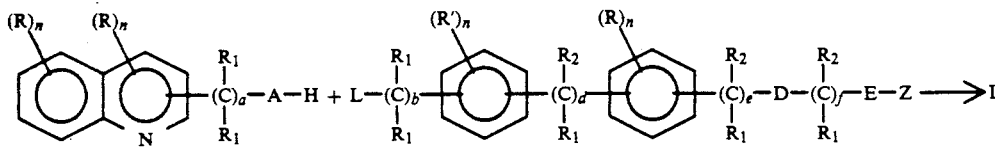

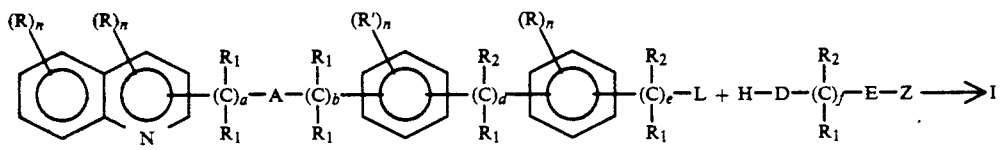

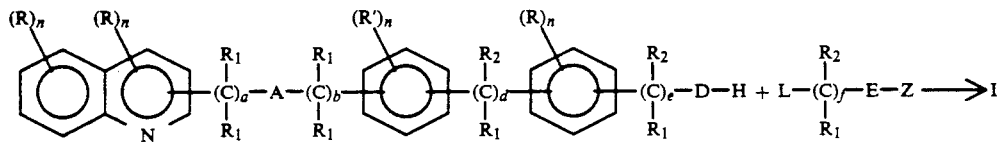

where:
R, R', $R_1$, $R_2$, a, b, d, e, f, n, A, and D are as defined above; E is a chemical bond; Z is —CN, —$COOR_1$ or tetrazolyl, and L is a leaving group, such as halo, tosylate, or mesylate.

Reaction temperatures are in the range of room temperature to reflux and reaction times vary from 2 to 48 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

Wittig condensation also may take place as follows:

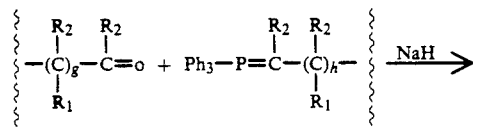

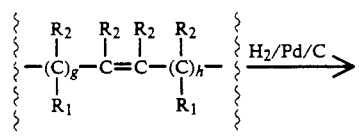

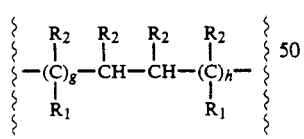

where g+h is 0-3

This may be carried out using normal Wittig reaction conditions. When the appropriate aldehyde or ketone is reacted with a Wittig reagent then condensation results in the formation of the double bond. This may then be reduced catalytically by known procedures such as Pd/C or any other suitable hydrogenating condition.

The Wittig reagent is prepared by known art recognized procedures such as reaction of triphenyl phosphine or triethyl phosphite, with a substituted alkyl bromide followed by treatment either with a strong organometallic or alkoxide base such as n-BuLi or NaOH, or heating to reflux for an appropriate period of time, respectively.

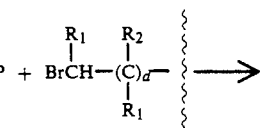

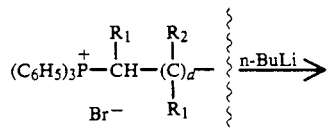

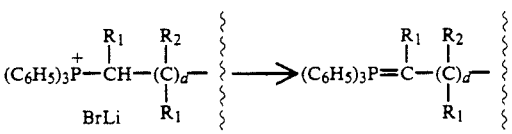

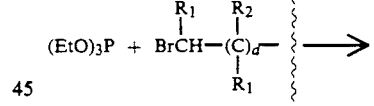

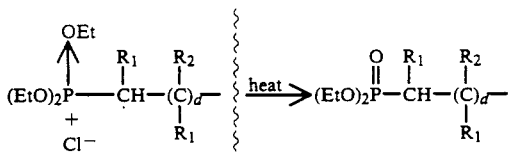

Those compounds where D and/or E

are also prepared by reacting the appropriate aldehyde or ketone with a substituted Wittig reagent of the formula

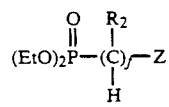

where Z is cyano or carbalkoxy.

The tetrazole may be formed from the nitrile at various stages of the synthesis by treatment with hydrazoic acid formed in situ from sodium azide and an acid.

The products of this invention may be obtained as racemic mixtures of their dextro and levorotatory isomers since at least one asymmetric carbon atom may be present. When two asymmetric carbon atoms are present the product may exist as a mixture of two disastereomers based on syn and anti configurations. These diastereomers may be separated by fractional crystallization. Each diastereomer may then be resolved into dextro and levorotatory optical isomers by conventional methods.

Resolution may best be carried out in the intermediate stage where it is convenient to combine the racemic compound with an optically active compound by salt formation, ester formation, or amide formation to form two disasteromeric products. If an acid is added to an optically active base, then two disastereomeric salts are produced which possess different properties and different solubilities and can be separated by fractional crystallization. When the salts have been completely separated by repeated crystallization, the base is split off by acid hydrolysis and the pure d and l acids are obtained.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, mailic, tartaric and the like which are pharmaceutically acceptable. Basic salts for pharmaceutical use are the Na, K, Ca and Mg salts.

Various substituents on the present new compounds, e.g., as defined in R, $R_1$ and $R_2$ can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel—Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones Thus, substitution or alteration reactions can be employed to provide a variety of substituents throughout the molecule of the starting material, intermediates, or the final product.

The compounds of the present invention have potent activity as leukotriene antagonists and as such possess therapeutic value in the treatment of inflammatory conditions and allergic responses such as anaphlaxis and asthma.

Protocol for SRS-A (slow reacting substance of anaphylaxis) Antagonists

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure - (Proc. Nat'l. Acad. Sci., U.S.A. Volume 77, pp. 4354–4358, 1980). The strips are thoroughly rinsed in Assay Buffer and then connected with surgical silk thread support rods from the tissue baths. The rods are adjusted in the baths and the strips connected to the pressure transducers (Grass FT 103 or Gould US-3). The tissue baths are aerated with 95% oxygen - 5% carbon dioxide and maintained at 37° C. The assay buffer has been made as follows: for each liter of buffer the following are added to approximately 800 ml of water distilled in glass-6.87 g NaCl, 0.4 g $MgSO_4.7H_2O$, and 2.0 g D-glucose. Then a solution of 0.368 g $CaCl_2.H_2O$ in 100 ml glass-distilled water is slowly added to the buffer. Sufficient water is added to adjust the volume to 1 liter, and the solution is aerated with 95% oxygen - 5% carbon dioxide. Usually 10 liters of buffer are used for an experiment with 4 tissues. After the tissues have been repeatedly washed and allowed to equilibrate in the tissue bath, they are challenged with 1 $\mu$M histamine. After maximum contractions have been obtained, the tissues are washed and allowed to relax back to baseline tension. This histamine challenge procedure is repeated at least 1 to 2 more times to obtain a repeatable control response. The average response to 1 $\mu$M histamine for each tissue is used to normalize all other challenges.

Responses of each tissue to a predetermined concentration of leukotriene are then obtained. Usually test compounds are examined initially at 30 $\mu$M on resting tension of the tissues without any added agonist or antagonist to determine if the compound has any possible intrinsic activity. The tissues are washed and the test compound is added again. Leukotriene is added after the desired preincubation time. The intrinsic activity of the compounds, and their effect on leikotriene-induced contractions are then recorded.

The results of this test for of the compounds of the this invention indicates that these compounds are considered to be useful leukotriene antagonists.

Inhibitions of ($^3$H)-LTD$_4$ Binding Membranes from Guinea Pig Lung.

A. Preparation of the Crude Receptor Fraction

This procedure was adapted from Mong et al. 1984. Male guinea pigs are sacrificed by decapitation and their lungs are quickly removed and placed in a beaker containing ice-cold homgenization buffer. The lungs are separated from connective tissue, minced with scissors, blotted dry and weighed. The tissue is then homogenized in 40 volumes (w/v) of homogenization buffer with a Polytron at a setting of 6 for 30 seconds The homogenate is centrifuged at 1000×g for 10 minutes (e.g. 3500 RPM, SS-34 Rotor). The supernatant is filtered through two layers of cheese cloth and centrifuged at 30,000×g for 30 minutes (e.g. 18,500 RPM SS-34 Rotor), after which the resulting pellet is resuspended in 20 volumes of assay buffer by hand homoginization using a Dounce homogenizer. The final pellet is resuspended in 10 volumes of assay buffer and kept at 4° C. until use.

B. Binding Assay:

Each assay tube (16×100 mm) contains the following:

490 μl Assay Buffer
10 μl Test compound or solvent
100 μl $^3$H-LTD$_4$ (ca. 17,500 DMP)
400 μl Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C Filter (25 mm diameter) which is sitting in a vacuum manifold (e.g., Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to equilibrate for 4–6 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 μM.

(c) Solvent Controls: If test compound is dissolved in a solvent, controls for both Total Binding and Non-Specific Binding containing solvent but no compounds are required.

The results of this test indicate that the compounds for this invention exhibit valuable properties which are useful in the treatment of inflammatory conditions and allergic responses.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, opthalmic, sublingual and buccal; topically including opthalmic, dermal, ocular, rectal and nasal inhalation via insufflation and aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propyl parabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatement with small dosages by small increments until the optimum effect under the circumstances is reached. The therapeutic dosage will generally be from 0.1 to 100 mM/day or from about 0.1 mg to about 50 mg/kg of body weight per day and higher although it may be administered in several different dosage units. Higher dosages are required for oral administration.

The compounds of the present invention may be prepared by the following representative examples.

EXAMPLE 1

Methyl 3-(4-Hydroxybenzyl)Benzoate

Methyl 3-(4-hydroxybenzoyl)benzoate (0.1 mol) in absolute ethanol (500 ml) is shaken under 50 psi of hydrogen in the presence of 10% palladium on carbon (2 g). After consumption of the starting material the suspension is filtered and evaporated to give methyl 3-(4-hydroxybenzyl)benzoate

EXAMPLE 2

When methyl 3-(4-hydroxybenzoyl)benzoate of Example 1 is replaced by the compunds of Table I below, then the corresponding product is prepared.

TABLE I ethyl 3-(4-hydroxybenzoyl)benzoate
methyl 2-(4-hydroxybenzoyl)benzoate
methyl 3-(3-hydroxybenzoyl)benzoate
methyl 4-(3-hydroxybenzoyl)benzoate
methyl 4-(4-hydroxybenzoyl)benzoate
methyl 3-(2-hydroxybenzoyl)benzoate
methyl 3-(4-methoxy-3-hydroxybenzoyl)benzoate
methyl 3-(3-methyl-4-hydroxybenzoyl)benzoate
methyl 3-(2-methyl-4-hydroxybenzoyl)benzoate
methyl 4-(3-methyl-4-hydroxybenzoyl)benzoate
methyl 3-(4-methyl-3-hydroxybenzoyl)benzoate
methyl 3-(5-methyl-3-hydroxybenzoyl)benzoate
methyl 3-(4-hydroxybenzoyl)-4-methylbenzoate
methyl 4-(4-hydroxybenzoyl)-2-methylbenzoate
methyl 4-(4-hydroxybenzoyl)-3-methylbenzoate
methyl 4-(4-hydroxybenzoyl)-2-methoxybenzoate
methyl 4-(4-hydroxybenzoyl)-3-methoxybenzoate
methyl 4-(4-hydroxybenzoyl)-5-methylbenzoate
methyl 3-(3-hydroxybenzoyl)-4-methoxybenzoate
methyl 3-(4-hydroxybenzoylmethyl)benzoate
methyl 3-(2-(4-hydroxybenzoyl)ethyl)benzoate
methyl 3-(1-(4-hydroxybenzoyl)ethyl)benzoate
methyl 3-(3-(4-hydroxybenzoyl)propyl)benzoate
methyl 3-(2-(4-hydroxybenzoyl)propyl)benzoate
methyl 3-(1-(4-hydroxybenzoyl)propyl)benzoate
methyl 3-(4-(4-hydroxybenzoyl)butyl)benzoate
methyl 3-(3-(4-hydroxybenzoyl)butyl)benzoate TABLE I-continued methyl 3-(2-(4-hydroxybenzoyl)butyl)benzoate
methyl 3-(1-(4-hydroxybenzoyl)butyl)benzoate
methyl 3-(4-(4-hydroxybenzoyl)-3,3-dimethylbutyl)-benzoate
methyl 3-(3-cyclopropyl-2-(4-hydroxybenzoyl)butyl)-benzoate
methyl 3-(2-phenyl-4-(4-hydroxybenzoyl)butyl)benzoate
methyl 4-(3-methoxy-2-(4-hydroxybenzoyl)propyl)-benzoate
methyl 4-(3-dimethylamino-2-(3-hydroxybenzoyl)propyl)-benzoate
methyl 4-(3-acetylamino-2-(3-hydroxybenzoyl)propyl)-benzoate
methyl 4-(3-spiro-1'-cyclopentane-2-(4-hydroxybenzoyl)propyl)benzoate
methyl 2-(3-carbomethoxy-2-(3-hydroxybenzoyl)propy)-benzoate
methyl 4-(3-benzylamino-2-(2-hydroxybenzoyl)butyl)-benzoate
methyl 3-(4-hydroxybenzoyl)phenoxyacetate
methyl 3-(4-hydroxybenzoyl)phenoxypropionate
methyl 4-(3-hydroxybenzoyl)phenoxyacetate
methyl 4-(3-hydroxybenzoyl)phenoxypropionate
methyl 3-(3-hydroxybenzoyl)phenoxyacetate
methyl 3-(3-hydroxybenzoyl)phenoxypropionate
methyl 4-(4-hydroxybenzoyl)phenoxyacetate
methyl 4-(4-hydroxybenzoyl)phenoxypropionate
methyl 3-(4-hydroxybenzoyl)phenylacetate
methyl 3-(4-hydroxybenzoyl)phenylpropionate
methyl 3-(4-hydroxybenzoyl)phenylbutyrate
methyl 3-(4-hydroxybenzoyl)benzonitrile
methyl 5-(3-(4-hydroxybenzoyl)phenyl)tetrazole
ethyl 4-(4-methoxy-3-hydroxybenzoyl)benzoate
methyl 4-(3-methoxy-4-hydroxybenzoyl)benzoate
methyl 3-(3-methyl-4-hydroxybenzoyl)-4-methylbenzoate
methyl 3-(4-hydroxybenzoyl)-4-methoxybenzoate
methyl 3-(4-hydroxybenzoyl)-5-methoxybenzoate
methyl 4-(4-hydroxybenzoyl)-2-methoxybenzoate
methyl 4-(4-hydroxybenzoyl)-3-carbomethoxybenzoate
methyl 3-(4-hydroxybenzoyl)-4-ethoxybenzoate
methyl 3-(4-mercaptobenzoyl)benzoate
methyl 4-(3-mercaptobenzoyl)benzoate
methyl 3-(3-mercaptobenzoyl)benzoate
methyl 4-(4-mercaptobenzoyl)benzoate
methyl 2-(4-mercaptobenzoyl)benzoate
methyl 3-(4-mercaptobenzoyl)benzoate

EXAMPLE 3

Methyl 3-(4-(2-Quinolinylmethyloxy)Benzyl)Benzoate

A mixture of methyl 3-(4-hydroxybenzyl)benzoate (0.08 mol), 2-chloromethylquinoline (0.10 mol) and potassium carbonate (anhydrous, 0.10 mol) are heated at reflux in a 7:1 mixture of acetone:dimethylformamide (600 ml) until all the benzoate starting material is consumed. The reaction is then filtered, evaporated and the residue diluted with water and extracted with ethyl acetate. The ethyl acetate extracts are dried (magnesium sulfate), evaporated and then applied to a silica gel column. Elution with ethyl acetate:petroleum ether gives methyl 3-(4-(2-quinolinylmethyloxy)benzyl)benzoate.

EXAMPLE 4

When 2-quinolinylmethyl chloride of Example 3 above is replaced by the quinoline compounds of Table II below then the corresponding product is obtained.

TABLE 2

2-chloromethylquinoline
2-bromomethylquinoline
2-(1-chloroethyl)quinoline
2-(2-chloroethyl)quinoline
2-bromoethylquinoline
3-chloromethylquinoline
4-chloromethylquinoline

TABLE 2-continued 2-(β-chloroethyl)quinoline
2-(β-chloropropyl)quinoline
2-(β-chloro-β-phenethyl)quinoline
2-chloromethyl-4-methylquinoline
2-chloromethyl-6-methylquinoline
2-chloromethyl-8-methylquinoline
2-chloromethyl-6-methoxyquinoline
2-chloromethyl-6-nitroquinoline
2-chloromethyl-6,8-dimethylquinoline

EXAMPLE 5

3-(4-(2-Quinolinylmethyloxy)Benzyl)Benzoic Acid

Methyl 3-(4-(2-quinolinylmethyloxy)benzyl)benzoate (0.05 mol) is heated at reflux in a 9:1 mixture of ethanol and 0.5 N aqueous NaOH (450 ml). After several hours the clear reaction is evaporated. The solid residue is taken up in water and acidified. The resulting crystalline product is isolated by filtration and dried by suction with a rubber dam to obtain 3-(4-(2-quinolinylmethyloxy)benzyl)benzoic acid.

In a similar manner the acids of this invention may be prepared.

EXAMPLE 6

3-(4-(2-Quinolinylmethyloxy)Benzyl)Benzoyl Chloride

To (0.05 mol) of 3-(4-(2-quinolinylmethyloxy)benzyl)benzoic acid in dichloromethane solution (500 ml) and chilled in an ice bath is added thionyl chloride (0.06 mol) and a few drops of dimethylformamide. Upon completion of the reaction, the clear solution is evaporated to give 3-(4-(2-quinolinylmethyloxy)benzyl)benzoyl choride.

In a similar manner the acid halides of this invention may be prepared.

EXAMPLE 7

3-(4-(2-Quinolinylmethyloxy)Benzyl)Benzamide 3-(4-(2-Quinolinylmethyloxy)benzyl)benzoyl chloride (0.05 mol) in tetrahydrofuran (300 ml) is treated with concentrated ammonium hydroxide (25 ml). The reaction mixture is stirred overnight at room temperature and then evaporated and partitioned between ethyl acetate and water. The ethyl acetate fraction is dried and evaporated to give 3-(4-(2-quinolinylmethyloxy)benzyl)benzamide.

In a similar manner the amides of this invention may be prepared.

EXAMPLE 8

3-(4-(2-Quinolinylmethyloxy)Benzyl)Benzonitrile 3-(4-(2-Quinolinylmethyloxy)benzyl)benzamide (0.03 mol) in pyridine (150 ml) with methane sulfonyl chloride (0.06 mol) is heated at 70° C. for several hours. The reaction mixture is poured into ice water and extracted with ethyl acetate. The ethyl acetate extract is dried (magnesium sulfate) then applied to a silica gel column. The product is isolated by elution with the appropriate mixture of ethyl acetate and petroleum ether to obtain 3-(4-(2-quinolinylmethyloxy)benzyl)benzonitrile.

In a similar manner the nitriles of this invention may be prepared.

EXAMPLE 9

5-(3-(4-(2-Quinolinylmethyloxy)Benzyl)Phenyl)Tetrazole

A mixture of sodium azide (0.03 mol), ammonium chloride (0.03 mol) and 3-(4-(2-quinolinylmethyloxy)benzyl)benzonitrile (0.01 mol) in dimethylformamide (20 ml) are heated at 100° C. for 18 hours. The reaction is poured into aqueous 10% sodium hydroxide solution and washed with ethyl acetate. The crystalline product is isolated by acidification and filtration to obtain 5-(3-(4-(2-quinolinylmethyloxy)benzyl)phenyl)tetrazole.

EXAMPLE 10

When the procedures of 1-9 are followed and the starting materials are selected from Table I of Example 2 and Table II of Example 4, then the corresponding products are obtained. A representative list of compounds so prepared are shown below in Table III.

TABLE III 5-(3-(3-(2-quinolinylmethyloxy)benzyl)phenyl]tetrazole
5-[3-(4-(2-quinolinylmethyloxy)benzyl)phenyl]tetrazole
5-[2-(4-(2-quinolinylmethyloxy)benzyl)phenyl]tetrazole
5-[4-(3-(2-quinolinylmethyloxy)benzyl)phenyl]tetrazole
5-[4-(4-(2-quinolinylmethyloxy)benzyl)phenyl]tetrazole
5-[2-(3-(2-quinolinylmethyloxy)benzyl)phenyl]tetrazole
5-[3-(3-(2-quinolinylmethyloxy)benzyl)benzyl]tetrazole
5-[4-(3-(2-quinolinylmethyloxy)benzyl)benzyl]tetrazole
5-[3-(4-(2-quinolinylmethyloxy)benzyl)benzyl]tetrazole
5-[2-(3-(2-quinolinylmethyloxy)benzyl)benzyl]tetrazole
5-[4-(4-(2-quinolinylmethyloxy)benzyl)benzyl]tetrazole
5-[2-(4-(2-quinolinylmethyloxy)benzyl)benzyl]tetrazole
5-[2-(3-(4-(2-quinolinylmethyloxy)benzyl)phenyl)propyl]tetrazole
5-[2-(3-(4-(2-quinolinylmethyloxy)benzyl)phenyl)butyl]tetrazole
5-[3-(3-(4-(2-quinolinylmethyloxy)benzyl)phenyl)butyl]tetrazole
5-[3-(3-(2-quinolinylmethylthio)benzyl)phenyl]tetrazole
5-[3-(3-(2-quinolinylmethylthio)phenethyl)phenyl]tetrazole
5-[3-(3-(2-quinolinylmethyloxy)phenylpropyl)phenyl]tetrazole
5-[4-(3-(2-quinolinylmethyloxy)phenylbutyl)-3-methoxyphenyl]tetrazole
5-[3-(3-(2-quinolinylmethyloxy)benzyl)-4-methoxyphenyl]tetrazole
5-[4-(4-(2-quinolinylmethyloxy)benzyl)-3-methoxyphenyl]tetrazole
5-[3-(4-(2-quinolinylmethyloxy)benzyl)-4-methoxyphenyl]tetrazole
5-[4-(3-(2-quinolinylmethyloxy)benzyl)-3-methoxyphenyl]tetrazole
5-[4-(3-(2-quinolinylmethyloxy)benzyl)-3-carbomethoxyphenyl]tetrazole
5-[4-(3-(2-quinolinylmethyloxy)benzyl)-3-methoxybenzyl]tetrazole
5-[3-(3-(2-quinolinylmethyloxy)benzyl)-4-methoxybenzyl]tetrazole
5-[3-(4-(2-quinolinylmethyloxy)benzyl)-4-methoxybenzyl]tetrazole
5-[4-(4-(2-quinolinylmethyloxy)benzyl)-3-methoxybenzyl]tetrazole
5-[4-(4-(2-quinolinylmethyloxy)benzyl)-3-carbomethoxybenzyl] tetrazole
5-[4-(3-(2-quinolinylmethyloxy)benzyl)-3-carbomethoxybenzyl]tetrazole
5-[4-(3-(2-quinolinylmethyloxy)-4-methylbenzyl)phenyl]tetrazole
5-[3-(4-(2-quinolinylmethyloxy)-3-methylbenzyl)phenyl]tetrazole
5-(3-methyl-4-(3-(2-quinolinylmethyloxy)phenethyl)phenyl)butyl)tetrazole
5-(2-(4-(2-quinolinylmethyloxy)phenethyl)phenyl)tetrazole
5-(4-(3-(2-quinolinylmethyloxy)phenethyl)phenyl)tetrazole
5-(3-(4-(2-quinolinylmethyloxy)phenethyl)phenyl)tetrazole
5-(4-(4-(2-quinolinylmethyloxy)phenethyl)phenyl)tetrazole
5-(3-(3-(2-quinolinylmethyloxy)phenethyl)phenyl)tetrazole
5-(2-(3-(2-quinolinylmethyloxy)phenethyl)phenyl)tetrazole TABLE III-continued 5-(2-(4-(2-quinolinylmethyloxy)phenethyl)benzyl)tetrazole
5-(3-(4-(2-quinolinylmethyloxy)phenethyl)benzyl)tetrazole
5-(4-(4-(2-quinolinylmethyloxy)phenethyl)benzyl)tetrazole
5-(2-(3-(2-quinolinylmethyloxy)phenethyl)benzyl)tetrazole
5-(3-(3-(2-quinolinylmethyloxy)phenethyl)benzyl)tetrazole
5-(4-(3-(2-quinolinylmethyloxy)phenethyl)benzyl)tetrazole

EXAMPLE 11

3-(2-Quinolinylmethloxy)Benzaldehyde

A solution of 0.65 g (5.4 mmol) 3-hydroxybenzaldehyde, 0.94 g (5.3 mmol) of 2-quinolinylmethylchloride, and 0.75 g (5.4 mmol) of potassium carbonate in 15 ml of DMF is heated at 60° C. overnight. The reaction mixture is poured into water. The precipitated product is collected on a filter and purified by dry column chromatography to give 3-(2-quinolinylmethyloxy)benzaldehyde.

EXAMPLE 12

When 3-hydroxybenzaldehyde of Example 11 is replaced by the compounds of Table IV below, then the corresponding product is obtained.

TABLE IV 2-hydroxybenzaldehyde
3-hydroxybenzaldehyde
4-hydroxybenzaldehyde
2-methyl-3-hydroxybenzaldehyde
5-methyl-3-hydroxybenzaldehyde
2-methyl-4-hydroxybenzaldehyde
3-methyl-4-hydroxybenzaldehyde
5-methoxy-3-hydroxybenzaldehyde
4-methoxy-3-hydroxybenzaldehyde
2-methoxy-3-hydroxybenzaldehyde
5-carbomethoxy-3-hydroxybenzaldehyde
3-hydroxyphenylacetaldehyde
4-hydroxyphenylacetaldehyde
3-hydroxyphenylpropionaldehyde
4-hydroxyphenylpropionaldehyde
3-hydroxyphenylisopropionaldehyde
4-hydroxyphenylisopropionaldehyde
3-hydroxyphenylbutyraldehyde
4-hydroxyphenylbutyraldehyde
3-mercaptobenzaldehyde
4-mercaptobenzaldehyde
3-hydroxyphenyl-α-methylbutyraldehyde
3-hydroxyphenyl-β-methylbutyraldehyde
4-hydroxyphenyl-α-methylbutyraldehyde
4-hydroxyphenyl-β-methylbutyraldehyde

EXAMPLE 13

When 2-quinolinylmethyl chloride of Examples 11 and 12 are replaced by the compounds of Example 4, Table II, then the corresponding products are obtained.

EXAMPLE 14

4-(3-(3-(2-Quinolinylmethyloxy)Phenyl)-1-Oxo-2-Propen-1-yl)Benzonitrile

4-Cyanoacetophenone (0.01 mol) in ethanol (100 ml) is added dropwise to a 0° C. mixture of 3-(2-quinolinylmethyl-oxy)benzaldehyde (0.01 mol) and sodium ethoxide (0.001 mol) in ethanol (200 ml). The reaction mixture is allowed to.thaw to ambient temperature and after several hours it is evaporated and partitioned between ethyl acetate and water. The ethyl acetate fraction is dried and evaporated to give 4-(3-(3-(2-quinolinylmethyloxy)phenyl)-1-oxo-2-propen-1-yl)benzonitrile.

EXAMPLE 15

When 3-(2-quinolinylmethyloxy)benzaldehyde of Example 14 is replaced by the compounds formed in Examples 12 and 13, then the corresponding product is obtained.

EXAMPLE 16

4-(3-(3-(2-Quinolinylmethyloxy)Phenyl)Propyl)Benzonitrile

A solution of 4-(3-(3-(2-quinolinylmethyloxy)phenyl)-1-oxo-2-propen-1-yl)benzonitrile (0.008 mol) in ethyl acetate (150 ml) is shaken under 50 psi of hydrogen gas in the presence of 10% palladium an carbon catalyst (1.0 g). The reaction is filtered through a celite pad and evaporated to give 4-(3-(3(2-quinolinylmethyloxy)phenyl)propyl)benzonitrile.

EXAMPLE 17

5-(4-(3-(3-2-Quinolinylmethyloxy)Phenyl)Propyl)-Phenyl)Tetrazole 4-(3-(3-(2-Quinolinylmethyloxy)phenyl)propyl)benzonitrile (0.006 mol) with sodium azide (0.018 mol) and ammonium chloride (0.018 mol) in dimethylformamide (15 ml) is heated at 100° C. for 18 hours. The reaction mixture is poured into 10% aqueous sodium hydroxide solution and washed with ethyl acetate. The aqueous layer is acidified to pH 6 with 1 N aqueous HCl and the solid which precipitates is collected to obtain 5-(4-(3-(3-(2-quinolinylmethyloxy)phenyl)propyl)phenyl)tetrazole.

EXAMPLE 18

When the compounds obtained in Example 13 are used as the starting materials in Example 14, then the corresponding producs are obtained. Representative compounds so obtained are shown in Table V, below.

TABLE V 5-(4-(3-(4-(2-quinolinylmethyloxy)phenyl)propyl)-phenyl)tetrazole
5-(3-(3-(2-quinolinylmethyloxy)phenyl)propyl)-phenyl)tetrazole
5-(2-(3-(4-(2-quinolinylmethyloxy)phenyl)propyl)-phenyl)tetrazole
5-(2-(3-(3-(2-quinolinylmethyloxy)phenyl)propyl)-phenyl)tetrazole
5-(3-(3-(4-(2-quinolinylmethyloxy)phenyl)propyl)-phenyl)tetrazole
5-(4-(4-(3-(2-quinolinylmethyloxy)phenyl)butyl)-phenyl)tetrazole
5-(4-(3-(3-(2-quinolinylmethyloxy)phenyl)butyl)-phenyl)tetrazole
5-(4-(2-(3-(2-quinolinylmethyloxy)phenyl)butyl)-phenyl)tetrazole
5-(3-(3-(4-(2-quinolinylmethyloxy)phenyl)butyl)-phenyl)tetrazole
5-(4-(4-(4-(2-quinolinylmethyloxy)phenyl)butyl)-phenyl)tetrazole
5-(3-(3-(3-(2-quinolinylmethyloxy)phenyl)butyl)-phenyl)tetrazole
5-(2-(4-(3-(4-(2-quinolinylmethyloxy)phenyl)propyl)-phenyl)ethyl)tetrazole
5-(3-(4-(3-(4-(2-quinolinylmethyloxy)phenyl)propyl)-phenyl)propyl)tetrazole
5-(2-(4-(3-(4-(2-quinolinylmethyloxy)phenyl)propyl)-phenyl)propyl)tetrazole
5-(3-(2-quinolinylmethyloxy)α-methylphenethyl)-phenyl)tetrazole
5-(3-(3-(2-quinolinylmethyloxy)β-methylphenethyl)-phenyl)tetrazole
5-(4-(3-(2-quinolinylmethyloxy)α-methylphenethyl)-phenyl)tetrazole
5-(4-(3-(2-quinolinylmethyloxy)β-methylphenethyl)-

TABLE V-continued phenyl)tetrazole
5-(4-(4-(2-quinolinylmethyloxy)α-methylphenethyl)-phenyl)tetrazole
5-(4-(4-(2-quinolinylmethyloxy)β-methylphenethyl)-phenyl)tetrazole
5-(3-(4-(2-quinolinylmethyloxy)α-methylphenethyl)-phenyl)tetrazole
5-(3-(4-(2-quinolinylmethyloxy)β-methylphenethyl)-phenyl)tetrazole
5-(3-(3-(2-quinolinylmethyloxy)α-methylphenethyl)-benzyl)tetrazole
5-(3-(3-(2-quinolinylmethyloxy)β-methylphenethyl)-benzyl)tetrazole
5-(4-(3-(2-quinolinylmethyloxy)α-methylphenethyl)-benzyl)tetrazole
5-(3-(4-(2-quinolinylmethyloxy)β-methylphenethyl)-benzyl)tetrazole
5-(4-(4-(2-quinolinylmethyloxy)α-methylphenethyl)-benzyl)tetrazole
5-(4-(3-(2-quinolinylmethyloxy)benzyl)phenyl)-tetrazole
5-(4-(3-(2-quinolinylmethyloxy)phenethyl)phenyl-tetrazole
5-(4-(3-(2-quinolinylmethyloxy)phenethyl)benzyl)-tetrazole
5-(4-(3-(2-quinolinylmethyloxy)phenethyl)phenethyl-tetrazole
5-(4-(3-(2-quinolinylmethyloxy)benzyl)benzyl)-tetrazole
5-(4-(3-(2-quinolinylmethyloxy)phenethyl)phenethyl-tetrazole
5-(4-(3-(3-(2-quinolinylmethyloxy)phenyl)propyl)-benzyl)tetrazole
5-(4-(3-(4-(2-quinolinylmethyloxy)phenyl)propyl)-benzyl)tetrazole
5-(4-(4-(3-(4-(2-quinolinylmethyloxy)phenyl)propyl)-phenyl)butyl)tetrazole
5-(3-(4-(3-(4-(2-quinolinylmethyloxy)phenyl)propyl)-phenyl)butyl)tetrazole
5-(2-(4-(3-(4-(2-quinolinylmethyloxy)phenyl)propyl)-phenyl)butyl)tetrazole

EXAMPLE 19

4-(4-(2-Quinolinylmethyloxy)Styryl)Benzonitrile

A suspension of 5.51 g (13.29 mmol) of (4-cyanobenzyl)triphenylphosphonium chloride in 100 ml of dry DMF under positive nitrogen atmosphere is cooled to 0° C. and 0.50 g (20.77 mmol), of an 80% NaH in oil dispersion is added in small portions. The suspension is aged for 15 minutes at 0° C. followed by 45 minutes at room temperature to assure complete anion formation. The flask is cooled back to 0° C. and 3.5 g (13.29 mmol) of 4-(2-quinolinylmethyloxy)benzaldehyde in 20 ml of DMF is dropped in over a period of 15 minutes. The reaction is allowed to equilibrate to room temperature and stirred for 2 hours. The resultant mixture is poured into ice water and filtered. The precipitate is dissolved in CH$_2$Cl$_2$, dried, and concentrated in vacuo. The crude product is recrystallized from ether to give 4-(4-(2-quinolinylmethyloxy)styryl)benzonitrile. (M.P. 116° C.-118° C.)

EXAMPLE 20

When (4-cyanobenzyl)triphenylphosphonium chloride of Example 19 is replaced by the compounds of Table VI below then the corresponding products are prepared.

TABLE VI 2-cyanobenzyl triphenylphosphonium chloride
3-cyanobenzyl triphenylphosphonium chloride
4-cyanobenzyl triphenylphosphonium chloride
3-cyano-4-methylbenzyl triphenylphosphonium chloride

TABLE VI-continued 4-cyano-3-methylbenzyl triphenylphosphonium chloride
3-cyanomethylbenzyl triphenylphosphonium chloride
4-cyanomethylbenzyl triphenylphosphonium chloride
3-cyanoethylbenzyl triphenylphosphonium chloride
4-cyanoethylbenzyl triphenylphosphonium chloride
3-cyanopropylbenzyl triphenylphosphonium chloride
4-cyanopropylbenzyl triphenylphosphonium chloride
3-(2-cyanopropyl)benzyl triphenylphosphonium chloride
4-(2-cyanopropyl)benzyl triphenylphosphonium chloride
3-(2-cyanobutyl)benzyl triphenylphosphonium chloride
4-(2-cyanobutyl)benzyl triphenylphosphonium chloride
3-(3-cyanobutyl)benzyl triphenylphosphonium chloride
4-(3-cyanobutyl)benzyl triphenylphosphonium chloride
3-cyanophenylethyl triphenylphosphonium chloride
4-cyanophenylethyl triphenylphosphonium chloride
3-(2-cyanopropylthio)benzyl triphenylphosphonium chloride
3-(2-cyanopropyloxy)benzyl triphenylphosphonium chloride
3-(2-cyanopropyl-N-methylamino)benzyl triphenyl-phosphonium chloride
3-(3-cyanopropyloxy)benzyl triphenylphosphonium chloride

EXAMPLE 21

When the Wittig reagents of Table VI, Example 20 are reacted with the compunds prepared by Example 13 following the procedure of Example 19 then the corresponding products are obtained.

EXAMPLE 22

4-(4-(2-Quinolinylmethyloxy)Phenethyl)Benzonitrile

A mixture of 0.75 g (2.07 mmol) of (4-(4-(2-quinolinylmethyloxy)styryl)benzonitrile and 0.08 g of 10% Pd on carbon in 75 ml of ethanol is shaken for 1.5 hours under 30 PSI of hydrogen. The mixture is filtered through a bed of celite and the filtrate concentrated in vacuo. Trituration with ether gives a precipitate which is filtered off and recrystalized from methylene chloride-ether to give 4-(4-(2-quinolinylmethyloxy)phenethyl)benzonitrile. (M.P. 156° C.-158° C.)

EXAMPLE 23

5-(4-(4-(2-Quinolinylmethyloxy)Phenethyl)Phenyl)Tetrazole

A mixture of 0.35 g (0.96 mmol) of 4-(4-(2-quinolinylmethyloxy)phenethyl)benzonitrile, 0.31 g (4.8 mmol, 5 equiv.) of sodium azide, and 0.55 g (4.8 mmol, 5 equiv.) of pyridine hydrochloride in 15 ml of DMF are heated at 110° C. for 48 hours. The mixture is poured into ice water and the precipitate that forms filtered off and recrystallized from methanol-water to obtain 5-(4-(4-(2-quinolinylmethyloxy) phenethyl)phenyl)tetrazole. (M.P. 203° C.-206° C.)

EXAMPLE 24

When the procedures of Examples 22 and 23 are followed using the compounds prepared by Examples 20 and 21 as the starting materials, then the corresponding products are obtained. A representative list of the compounds thus prepared is shown in Table VII below.

TABLE VII 5-(4-(4-(3-(2-quinolinylmethyloxy)phenethyl)phenyl)-butyl)tetrazole
5-(3-(4-(3-(2-quinolinylmethyloxy)phenethyl)phenyl)-butyl)tetrazole
5-(3-(4-(4-(2-quinolinylmethyloxy)phenethyl)phenoxy)-

TABLE VII-continued butyl)tetrazole
5-(2-(3-(3-(2-quinolinylmethyloxy)phenethyl)phenoxy)propyl)tetrazole
5-(3-(3-(2-quinolinylmethylthio)phenethyl)phenylthio)butyl)tetrazole
5-(3-(3-(2-quinolinylmethylthio)phenethyl)phenoxy)butyl)tetrazole
5-(3-(3-(2-quinolinylmethyloxy)phenethyl)phenethyl)tetrazole
5-(3-(3-(2-quinolinylmethyloxy)benzyloxy)phenethyl)tetrazole
5-(3-(3-(3-(2-quinolinylmethyloxy)phenyl)propyl)phenyl)butyl)tetrazole
5-(2-(3-(2-quinolinylmethyloxy)benzyl)phenoxymethyl)tetrazole
5-(3-(3-(2-quinolinylmethyloxy)benzyl)phenoxymethyl)tetrazole
5-(4-(3-(2-quinolinylmethyloxy)benzyl)phenoxymethyl)tetrazole
5-(2-(4-(2-quinolinylmethyloxy)benzyl)phenoxymethyl)tetrazole
5-(3-(4-(2-quinolinylmethyloxy)benzyl)phenoxymethyl)tetrazole
5-(4-(4-(2-quinolinylmethyloxy)benzyl)phenoxymethyl)tetrazole
5-(3-(3-(2-quinolinylmethyloxy)benzyl)phenoxyethyl)tetrazole
5-(3-(4-(2-quinolinylmethyloxy)benzyl)phenoxyethyl)tetrazole
5-(4-(3-(2-quinolinylmethyloxy)benzyl)phenoxyethyl)tetrazole
5-(4-(4-(2-quinolinylmethyloxy)benzyl)phenoxyethyl)tetrazole
5-(3-(3-(2-quinolinylmethyloxy)phenethyl)phenoxymethyl)tetrazole
5-(4-(3-(2-quinolinylmethyloxy)phenethyl)phenoxymethyl)tetrazole
5-(3-(4-(2-quinolinylmethyloxy)phenethyl)phenoxymethyl)tetrazole
5-(4-(4-(2-quinolinylmethyloxy)phenethyl)phenoxymethyl)tetrazole
5-(3-(3-(2-quinolinylmethyloxy)phenethyl)phenoxyethyl)tetrazole
5-(4-(3-(2-quinolinylmethyloxy)phenethyl)phenoxyethyl)tetrazole
5-(3-(4-(2-quinolinylmethyloxy)phenethyl)phenoxyethyl)tetrazole
5-(4-(4-(2-quinolinylmethyloxy)phenethyl)phenoxyethyl)tetrazole

EXAMPLE 25

3-(4-(2-Quinolinylmethyloxy)Benzyl)Benzoyl-N-Benzenesulfonamide

A reaction mixture of 0.65 g of 3-(4-(2-quinolinylmethyloxy)benzyl)benzoic acid, 0.28 g of benzenesulfonamide, 0.28 g of 4-dimethylpyridine, and 0.44 g of 1-(3-dimethylaminopropyl)-3-ethylcarbodimidehydrochloride in 50 ml of $CH_2Cl_2$ is stirred at room temperature overnight. The solvent is removed and the residue is extracted into ethyl acetate. The organic solution is washed with water, and evaporated. The product is purified by dry column chromatography to give 3-(4-(2-quinolinylmethyloxy)benzyl)benzoyl-N-benzenesulfonamide.

EXAMPLE 26

When 3-(4-(2-quinolinylmethyloxy)benzyl)benzoic acid of Example 25 is replaced by the acids of this invention such as those of Example 5 then the corresponding benzenesulfonamide compound is prepared.

When benzenesulfonamide is replaced in the above Examples by a sulfonamide of the formula $NH_2SO_2R_3$ or an amine of the formula $HN(R_1)_2$, then the corresponding product is obtained.

EXAMPLE 27

3-(3-(2-Quinolinylmethyloxy)Benzyl)Benzaldehyde

A solution of diisobutyl aluminum hydride (0.01 mol) in hexane is added dropwise to a solution of methyl 3-(3-(2-quinolinylmethyloxy)benzyl)benzoate (0.01 mol) in 100 ml of THF at 0° C. The reaction mixture is stirred at 0° C. for 30 minutes and then quenched with methanol and Rochelle salt. Extraction with ethyl acetate and purified by column chromatography gives 3-(3-(2-quinolinylmethyloxy)benzyl)benzaldehyde.

EXAMPLE 28

When the esters of Examples 3 and 4 are used in place of methyl 3-(3-(2-quinolinylmethyloxy)benzyl)benzoate in Example 27 then the corresponding aldehyde is obtained.

EXAMPLE 29

3-(3-(2-Quinolinylmethyloxy)Benzyl)Cinnamylnitrile

Sodium hydride (60% oil dispersion, 1.2 g) and diethyl cyanomethylphosphonate (5 ml) are combined and stirred in THF (50 ml) for 5 minutes. This is then added to a THF solution of 3-(3-(2-quinolinylmethyloxy)benzyl)benzaldehyde (9.5 g). The reaction mixture is stirred for an additional 30 minutes and poured into ice water. The crude product is filtered and chromatographed through a silica gel dry column using chloroform as the eluant to give 3-(3-(2-quinolinylmethyloxy)benzyl)cinnamylnitrile.

EXAMPLE 30

When 3-(3-(2-quinolinylmethyloxy)benzyl)benzaldehyde of Example 29 is replaced by the compounds of Example 28, the corresponding product is prepared.

When diethylcyanomethylphosphonate in the above Example is replaced by diethylcyanoethylphosphate, diethylcyanopropylphospate or diethylcyanoisopropylphosphate then the corresponding products are obtained.

EXAMPLE 31

5-(3-(3-(2-Quinolinylmethyloxy)Benzyl)Styrltetrazole Hydrochloride

A mixture of 3-(3-(2-quinolinylmethyl)benzyl)cinnamylnitrile (0.03 mol), anhydrous aluminum chloride (0.03 mol) and sodium azide (0.09 mol) in THF (30 ml) is stirred and refluxed for 18 hours. Hydrochloric acid (18% HCl 15 ml) is added and thereafter the reaction mixture is poured into ice water. The precipitate is collected and then recrystalized from methanol-ethyl acetate to obtain pure 5-(3-(3-(2-quinolinylmethyloxy)benzyl)styryl)tetrazole hydrochloride.

The free base is obtained by treatment of the salt with one equivalent of sodium hydroxide solution followed by removal of sodium chloride and water.

EXAMPLE 32

When 3-(3-(2-quinolinylmethyloxy)benzyl)cinnamylnitrile of Example 31 is replaced by the compounds formed in Example 30, then the corresponding product rs prepared. Representative compounds prepared by this invention are described in Table VIII.

TABLE VIII 5-(4-(3-(2-quinolinylmethyloxy)benzyl)styryl)tetrazole
5-(4-(3-(2-quinolinylmethyloxy)phenethyl)styryl)tetrazole

TABLE VIII-continued 5-(3-(4-(2-quinolinylmethyloxy)benzyl)styryl)tetrazole
5-(4-(2-quinolinylmethyloxy)benzyl)styryl)tetrazole
5-(4-(3-(2-quinolinylmethyloxy)-4-methylbenzyl)styryl)-
  tetrazole
5-(4-(3-(2-quinolinylmethyloxy)benzyl)3-methyl)styryl)-
  tetrazole
5-(3-(3-(2-quinolinylmethylthio)benzyl)styryl)tetrazole
5-(3-(4-(2-quinolinylmethylthio)phenethyl)styryl)tetrazole
5-(3-(3-(4-(2-quinolinylmethyloxy)phenyl)propyl)styryl)-
  tetrazole
5-(3-(4-(3-(2-quinolinylmethyloxy)benzyl)phenoxy)2-propen-
  1-yl)tetrazole

EXAMPLE 33

Ethyl 5-(4-(3-(2-Quinolinylmethyloxy)Phenethyl)Phenyl)Tetrazol-3-yl Acetate

To a solution of 0.2 g sodium in 30 ml ethanol is first added 1 g of 5-(4-(3-(2-quinolinylmethyloxy)phenethyl)phenyl)tetrazole and then after 30 minutes 0.6 g of ethylbromacetate and stirring is continued at 80° C. for 16 hours. The solvent is then removed, diluted with water, filtered, washed with ether and dried to give ethyl 5-(4-(3-(2-quinolinylmethyloxy)phenethyl)-phenyl)tetrazol-3-yl acetate.

When ethylbromoacetate in the above procedure is replaced with N,N-diethyl-α-bromoacetamide, N,N-diethyl- aminoethyl bromide or N-acetylaminoethyl bromide or N- acetyl-α-bromoacetamide, then the corresponding products are obtained.

EXAMPLE 34

5-(4-(3-(2-Quinolinylmethyloxy)Phenethyl)Phenyl)Tetrazol-3-yl Acetic Acid

A mixture of 1 g of ethyl [5-(4-(3-(2-quinolinylmethyloxy)phenethyl)phenyl)tetrazol-3-yl]acetate in 5 ml ethanol and 40 ml of 1N NaOH is stirred at 70° C. for 4 hours. This is cooled, diluted with water, acidified with acetic acid, filtered, washed with water, and then ethyl acetate to give 5-(4-(3-(2-quinolinylmethyloxy)phenethyl)phenyl)tetrazol-3-yl acetic acid.

In a similar manner the substituted tetrazoles of this invention may be prepared.

EXAMPLE 35

4-(4-(2-Quinolinylmethylsulfinyl)Phenethyl)Benzoic Acid

A. 4-(4-(2-quinolinylmethylthio)phenethyl)benzoic acid (4 mmol) in dichloroethene (50 ml) is stirred with m-chloroperbenzoic acid (4 mmol) and solid potassium hydrogen carbonate (1.0 g). The reaction is assayed by TLC and upon consumption of the starting thio compound, the mixture is filtered, washed with dilute aqueous sodium bisulfite, dried and evaporated to give 4-(4-(2-quinolinylmethylsulfinyl)phenethyl)benzoic acid.

B. To 3 mmol of the sulfinyl compound from Step A in acetic acid (40 mmol) is added 30% hydrogen peroxide (2 ml). The mixture is stirred at ambient temperature and assayed by TLC. Upon disappearance of the sulfinyl starting compound, the reaction mixture is diluted with dichloromethane, washed with dilute aqueous sodium bisulfite and water, dried and evaporated to give 4-(4-(2-quinolinylmethylsulfonyl)phenethyl)benzoic acid.

In a similar manner the sulfinyl and sulfonyl compounds of this invention may be prepared.

EXAMPLE 36

4-(3-(3-(2-Quinolinylmethyloxy)Phenyl)-1-Oxo-2-Propen-1-yl)Phenol

4-Hydroxyacetophenone (0.01 mol) in ethanol (100 ml) is added dropwise to a 0° C. mixture of 3-(2-quinolinylmethyloxy)benzaldehyde (0.01 mol) and sodium ethoxide (0.00 mol) in ethanol (200 ml). The reaction mixture is allowed to thaw to ambient temperature and after several hours it is evaporated and partitioned between ethyl acetate and water. The ethyl acetate fraction is dried and evaporated to give 4-(3-(3-(2-quinolinylmethyloxy)phenyl)-1-oxo-2-propen-1-yl)phenol.

EXAMPLE 37

When 4-hydroxy acetophenone of Example 36 is replaced with the compounds of Table IX below, then the corresponding phenol is prepared.

TABLE IX 2-hydroxyacetophenone
3-hydroxyacetophenone
4-hydroxyacetophenone
3-methyl-4-hydroxyacetophenone
4-methyl-3-hydroxyacetophenone
2-methyl-4-hydroxyacetophenone
4-methoxy-3-hydroxyacetophenone
4-methoxy-2-hydroxyacetophenone
3-methoxy-4-hydroxyacetophenone
2-methoxy-4-hydroxyacetophenone
2-hydroxymethylacetophenone
3-hydroxymethylacetophenone
4-hydroxymethylacetophenone
3-hydroxypropylacetophenone
4-hydroxypropylacetophenone
3-hydroxyisopropylacetophenone
4-hydroxyisopropylacetophenone
3-hydroxybutylacetophenone
4-hydroxybutylacetophenone
2-hydroxybutylacetophenone
3-(2-methyl)hydroxybutylacetophenone
3-(3-methyl)hydroxybutylacetophenone
4-(2-methyl)hydroxybutylacetophenone
4-(3-methyl)hydroxybutylacetophenone

EXAMPLE 38

When 3-(2-quinolinylmethyloxy)benzaldehyde of Example 36 is replaced by the compounds formed in Examples 12 and 13 then the corresponding product is obtained.

EXAMPLE 39

4-(3-(3-(2-Quinolinylmethyloxy)Phenyl)Propyl)Phenol

A solution of 4-(3-(3-(2-quinolinylmethyloxy)-phenyl)-1-oxo-2-propen-1-yl)phenol (0.008 mol) in ethyl acetate (150 ml) is shaken under 50 psi of hydrogen gas in the presence of 10% palladium on carbon catalyst (1.0 g). The reaction mixture is filtered through a celite pad and evaporated to give 4-(3(3-(2-quinolinylmethyloxy)phenyl)propyl)phenol.

EXAMPLE 40

When 4-(3-(3-(2-quinolinylmethyloxy)phenyl)-1-oxo-2-propen-1-yl)phenol of Example 39 is replaced by the products prepared by Example 38, then the corresponding phenol is prepared.

EXAMPLE 41

5-(3-Chloropropyl)Tetrazole

A mixture of 3.5 g of 4-chlorobutyronitrile, 2.3 g of sodium azide and 1.9 g of ammonium chloride in 50 ml of dimethylformamide is stirred at 140° C. for 20 hours. The reaction mixture is poured onto ice, basified with 1N sodium hydroxide and extracted twice with ethyl acetate. The aqueous fraction is acidified with acetic acid and extracted with ethylacetate. Evaporation of the ethyl acetate gives 5-(3-chloropropyl)tetrazole which is used directly in the next step.

EXAMPLE 42

When 4-chlorobutyronitrile of Example 41 above is replaced by the nitriles of Table X below then the corresponding tetrazole product is obtained

TABLE X chloroacetonitrile
bromoacetonitrile
3-chloropropionitrile
4-chlorobutyronitrile
5-chloropentanonitrile
6-chlorohexanonitrile
2-chlorporopionitrile
2-methyl-3-chloropropionitrile
2-chlorobutyronitrile
3-chlorobutyronitrile
4-methyl-5-chloropentanonitrile
2-methyl-3-chloropropionitrile
3-benzyl-4-chlorobutyronitrile
3-carbethoxymethyl-4-chlorobutyronitrile
3-methoxymethyl-4-chlorobutyronitrile
2,3-dimethyl-4-chloropentanonitrile
3,3-dimethyl-4-chloropentanonitrile
sprio-(3,3-cyclopropane)-4-chlorobutyronitrile
1-chloromethyl-2-cyanomethylcyclobutane
1-chloromethyl-2-cyanomethylcyclohexane
3-cyclopropylmethyl-4-chlorobutyronitrile
3-dimethylaminomethyl-4-chlorobutyronitrile
3-methylene-4-chlorobutyronitrile
3-propylidene-4-chlorobutyronitrile

EXAMPLE 43

5-(3-(4-(3-(3-(2-Quinolinylmethyloxy)Phenyl)Propyl)-Phenoxy)Propyl)Tetrazole A mixture of (0.014 mol) 4-(3-(3-(2-quinolinylmethyloxy)benzyloxy)phenyl)propyl)phenol (0.14 mol) 5-(3-chloropropyl)tetrazole and 2 g (0.036 mol) KOH in 5 ml water and 50 ml ethanol is heated over a steam bath for a period of 3 hours. Reaction mixture is concentrated to dryness and slurried into water and extracted wtih methylene chloride. The methylene chloride extract is washed with water, dried over MgSO4 and concentrated under reduced pressure to obtain solid which is passed through a silica gel column using hexane/ethyl acetate as eluent. Evaporation of eluent gives 5-(3-(4-(3-(3-(2-quinolinylmethyloxy)phenyl)propyl)-phenoxy)propyl)tetrazole.

EXAMPLE 44

When 4-(3-(3-(3-(2-quinolinylmethyloxy)phenyl)-propyl)phenol of Example 40 is replaced by the compounds prepared by Examples 39 and 40 and 5-(3-chloropropyl)tetrazole is replaced by the compounds prepared by Example 42, then the corresponding product is obtained. A representative list of compounds so prepared is shown below in Table XI.

TABLE XI 5-(4-(3-(2-quinolinylmethyloxy)phenethyl)phenoxymethyl)tetrazole
5-(3-(3-(2-quinolinylmethyloxy)phenethyl)phenoxymethyl)tetrazole
5-(3-(4-(2-quinolinylmethyloxy)phenethyl)phenoxymethyl)tetrazole
5-(2-(3-(2-quinolinylmethyloxy)phenethyl)phenoxymethyl)tetrazole
5-(4-(3-(2-quinolinylmethyloxy)phenethyl)-phenoxymethyl)tetrazole
5-(2-(3-(3-(2-quinolinylmethyloxy)phenethyl)-phenoxy)propyl)tetrazole
5-(2-(3-(4-(2-quinolinylmethyloxy)phenethyl)-phenoxy)ethyl)tetrazole
5-(4-(2-(4-(3-quinolinylmethyloxy)phenethyl)-phenoxy)butyl)tetrazole

EXAMPLE 45

3-(4-(2-Quinolinylmethyloxy)Benzyl)Benzyl Alcohol

Methyl 3-(4-(2-quinolinylmethyloxy)benzyl)benzoate (0.002 mol) in tetrahydrofuran (50 ml) is added dropwise to a tetrahydrofuran (50 ml) suspension of lithium aluminium hydride (0.004 mol). After consumption of the ester, the remaining lithium aluminum hydride is quenched by the addition of water and filtration to remove the resulting salts. Evaporation of the solvent gives 3-(4-(2-quinolinylmethyloxy)benzyl)benzyl alcohol.

EXAMPLE 46

3-(4-(2-Quinolinylmethyloxy)Benzyl)Benzyl Alcohol Mesylate

To methanesulfonyl chloride (0.002 mol) and triethylamine (0.002 mol) in dichloromethane (40 ml) at 0° C. is added 3-(4-(2-quinolinylmethyloxy)benzyl)benzyl alcohol (0.0018 mol) in dichloromethane (40 ml) dropwise. After 24 hours, the reaction mixture is washed with water, dried and evaporated to give 3-(4-(2-quinolinylmethyloxy)benzyl)benzyl alcohol mesylate.

EXAMPLE 47

3-(4-(2-Quinolinylmethyloxy)Benzyl)Phenylacetonitrile 3-(4-(2-Quinolinylmethyloxy)benzyl)benzyl alcohol mesylate (0.0018 mol) with sodium cyanide (0.0036 mol) in dimethylsulfoxide (10 ml) is stirred at ambient temperature. After the consumption of sulfate, the reaction is diluted with water and extracted with ethyl acetate. The organic extracts are dried and evaporated to give 3-(4-(2-quinolinylmethyloxy)benzyl)phenylacetonitrile.

EXAMPLE 48

5-(3-(4-(2-Quinolinylmethyloxy)Benzyl)Benzyl)Tetrazole

Sodium azide (0.0054 mol), ammonium chloride (0.00..54 mol) 3-(4-(2-quinolinylmethyloxy)benzyl)-phenylacetonitrile in dimethylformamide (5 ml) are heated at 110° C.-115° C. for 24 hours. The product is isolated by pouring the reaction mixture into 10% sodium hdyroxide solution, washing with ethyl acetate, and inducing the crystallization by acidification with aqueous hydrogen chloride. This results in 5-(3-(4-(2-quinolinylmethyloxy)benzyl)benzyl)tetrazole.

The methods described above are used to prepare the following compounds of this invention.

5-[3-Methoxy-4-(3-(2-Quinolinylmethoxy)phenethyl)phenyl]tetrazole (M.P. 151°-154° C.). CALC: C, 67.84; H, 5.56; N, 15.20. FOUND: C, 68.02; H, 5.62; N, 14.75.

2-[4-(2-Quinolinylmethoxy)phenethyl]phenyl acetic acid (M.P. 174°-176° C.). CALC: C, 77.69; H, 5.89; N, 3.48. FOUND: C, 77.94; H, 6.11; N, 3.41.

2-[4-(2-Quinolinylmethoxy)benzyl]phenyl acetic acid (M.P. 183°-186° C.). CALC: C, 77.40; H, 5.58; N, 3.61. FOUND: C, 77.19; H, 5.84; N, 3.56.

5-[3-(4-(2-Quinolinylmethoxy)phenylpropan-2-yl)phenyl]tetrazole (M.P. 170°-173° C.). CALC: C, 73.30; H, 5.56; N, 16.44. FOUND: C, 73.05; H, 5.85; N, 16.16.

5-[3-(3-(2-Quinolinylmethoxy)phenethyl)benzyl]tetrazole (M.P. 53°-55° C.). CALC: C, 72.53; H, 5.62; N, 16.26. FOUND: C, 73.08; H, 5.68; N, 15.40.

5-[3-(3-(2-Quinolinylmethoxy)phenylpropan-2-yl)phenyl]tetrazole (M.P. 83°-86° C.). CALC: C, 70.40; H, 5.78; N, 15.77. FOUND: C, 70.81; H, 5.85; N, 15.45.

5-[4-(4-(2-Quinolinylmethoxy)benzyl)phenyl]tetrazole (M.P. 206°-209° C.). CALC: C, 73.27; H, 4.87; N, 17.80. FOUND: C, 72.86; H, 4.97; N, 17.64.

5-[3-(4-(2-Quinolinylmethoxy)benzyl)phenyl]tetrazole (M.P. 186°-189° C.). CALC: C, 66.42; H, 5.45; N, 16.13. FOUND: C, 66.27; H, 5.09; N, 16.09.

5-[3-(3-(2-Quinolinylmethoxy)phenethyl)phenyl]tetrazole (M.P 126°-129° C.). CALC: C, 69.11, H, 5.57; N, 16.12. FOUND: C, 69.27; H, 5.54; N, 16.43.

5-[3-(4-(2-Quinolinylmethoxy)phenethyl)phenyl]tetrazole (M.P. 165°-168° C.). CALC: C, 72.09; H, 5.32; N, 16.81. FOUND: C, 72.44; H, 5.64; N, 16.70.

We claim:

1. A compound of the formula

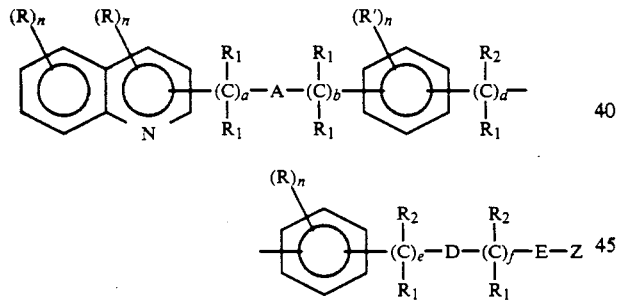

where:
A is O or S;
D is O, S, NR$_1$,

or a chemical bond
E is a chemical bond or

a is 0-2;
b is 0-1;
d is 1-5;
e is 0-4;
f is 0-5;
n is 0-2;

R is independently hydrogen, alkyl, hydroxy, alkoxy, carboxy, carbalkoxy, halo, nitro, haloalkyl, cyano or acyl;
R' is independently hydrogen, alkyl, hydroxy, alkoxy, halo or haloalkyl;
R$_1$ is independently hydrogen, alkyl or aralkyl;
R$_2$ is —(CH$_2$)$_x$—X;
x is 0-3;
X is hydrogen, alkyl, alkenyl, cycloalkyl, aryl, aralkyl, hydroxy, alkoxy, aralkoxy, amino, mono-and di-alkylamino, aralkylamino, acylamino, carbamyl, carboxy, carbalkoxy, tetrazolyl or acylsulfonamido;
vicinal R$_2$ groups together may be —(CH$_2$)$_y$—, where y is 1-4, thus forming a 3-6 membered ring;
geminal R$_1$ and R$_2$ groups may together form a spiro substituent, —(CH$_2$)$_z$—, where z is 2 to 5;
geminal R$_1$ or R$_1$ and R$_2$ groups may together form an alkylidenyl substituent, =CHR$_1$;
Z is —COOR$_1$, CN,

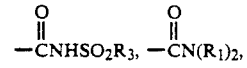

—OR$_1$, tetrazolyl or substituted tetrazolyl where the substituent may be alkyl, carboxyalkyl or carbalkoxyalkyl;
R$_3$ is hydrogen, alkyl, haloalkyl, phenyl or benzyl;
and pharmaceutically acceptable salts thereof.

2. A compound according to claim 1 where:
A is O or S;
n is 0-1;
a+b is 1;
e+f is 0-5;
R and R' are hydrogen, alkyl or alkoxy;
R$_1$ is hydrogen or alkyl;
R$_2$ is —(CH$_2$)$_x$—X;
x is 0-3;
X is hydrogen or alkyl; and
Z is —COOR$_1$, —CN,

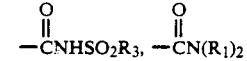

or tetrazolyl.

3. A compound according to claim 2 where:
A is O;
n is 0;
d is 1-3; and
Z is —COOR$_1$, —CN or tetrazolyl.

4. A compound according to claim 3 where:
a is 1;
b is 0; and
d is 1.

5. A compound according to claim 3 where:
a is 1;
b is 0; and
d is 2.

6. A compound according to claim 3 where:
a is 1;
b is 0; and
d is 3.

7. A compound according to claim 3 where:
D is O; and
E is a chemical bond.

8. A compound according to claim 3 where:

D is S; and

E is a chemical bond.

9. A compound according to claim 3 where:

e+f is 0;

D is a chemical bond; and

E is a chemical bond.

10. A compound according to claim 3 where:

e+f is 1-5;

D is a chemical bond; and

E is a chemical bond.

11. A compound according to claim 4 which is 5-(3-(3-(2-quinolinylmethyloxy)benzyl)phenyl)tetrazole.

12. A compound according to claim 5 which is 5-(4-(4-(2-quinolinylmethyloxy)phenethyl)phenyl)tetrazole.

13. A compound according to claim 5 which is 5-(4-(3-(2-quinolinylmethyloxy)phenethyl)phenyltetrazole.

14. A compound according to claim 4 which is 5-(3-methoxy-4-(3-(2-quinolinylmethyloxy)benzyl)phenyl)-tetrazole.

15. A compound according to claim 4 which is 5-(4-methoxy-3-(3-(2-quinolinylmethyloxy)benzyl)phenyl)-tetrazole.

16. A compound according to claim 4 which is 5-(4-(4-(2-quinolinylmethyloxy)benzyl)phenyl)tetrazole.

17. A compound according to claim 10 which is 5-(4-(4-(2-quinolinylmethyloxy)benzyl)benzyl)tetrazole.

18. A compound according to claim 10 which is 5-(4-(3-(4-(2-quinolinylmethyloxy)b.enzyl)phenyl)3-methyl-butyl)tetrazole.

19. A compound according to claim 5 which is 5-(3-(3-(2-quinolinylmethyloxy)phenethyl)phenyl)tetrazole.

20. A compound according to claim 5 which is 5-(2-(3-(2-quinolinylmethyloxy)phenethyl)phenyl)tetrazole.

21. A method for the treatment of hypersensitive ailments in humans and mammals comprising administering thereto an effective amount of a compound of the formula according to claim 1.

22. A pharmaceutical composition wherein the active ingredient is a compound according to claim 1 in admixture with a pharmaceutical carrier

* * * * *